United States Patent
Pursifull et al.

(10) Patent No.: US 9,482,172 B2
(45) Date of Patent: Nov. 1, 2016

(54) HUMIDITY SENSOR DIAGNOSTICS

(71) Applicant: Ford Global Technologies, LLC, Dearborn, MI (US)

(72) Inventors: Ross Dykstra Pursifull, Dearborn, MI (US); Imad Hassan Makki, Dearborn Heights, MI (US); Timothy Joseph Clark, Livonia, MI (US); Michael James Uhrich, West Bloomfield, MI (US); Pankaj Kumar, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 433 days.

(21) Appl. No.: 13/774,282

(22) Filed: Feb. 22, 2013

(65) Prior Publication Data
US 2014/0238370 A1    Aug. 28, 2014

(51) Int. Cl.
*F02D 41/22* (2006.01)
*F02D 41/00* (2006.01)

(52) U.S. Cl.
CPC ............ *F02D 41/222* (2013.01); *F02D 41/005* (2013.01); *F02D 2200/0418* (2013.01); *F02D 2200/0611* (2013.01); *Y02T 10/47* (2013.01)

(58) Field of Classification Search
CPC .................... F02D 2200/0418; F02D 41/222; F02D 41/005; F02D 2200/0414; F02D 41/0065; F02D 41/0245; F02D 41/064
USPC ........................................ 123/568.12–568.32
See application file for complete search history.

(56) References Cited

U.S. PATENT DOCUMENTS

| | | | |
|---|---|---|---|
| 6,073,480 A * | 6/2000 | Gokhfeld ............. | G01N 27/124 73/29.02 |
| 6,581,370 B2 | 6/2003 | Sato et al. | |
| 6,641,303 B2 | 11/2003 | Yamazaki et al. | |
| 6,725,848 B2 * | 4/2004 | Ramamurthy ........ | F02D 41/005 123/568.22 |
| 6,860,143 B2 | 3/2005 | Yamazaki et al. | |
| 7,176,700 B2 | 2/2007 | Itakura et al. | |
| 7,715,976 B1 | 5/2010 | Xiao et al. | |
| 8,543,317 B2 * | 9/2013 | Pasero .................. | F02D 41/005 123/568.22 |

(Continued)

OTHER PUBLICATIONS

Pursifull R., et al., "Humidity Sensor Diagnostics," U.S. Appl. No. 13/774,319, filed Feb. 22, 2013, 46 pages.

(Continued)

*Primary Examiner* — Sizo Vilakazi
(74) *Attorney, Agent, or Firm* — Julia Voutyras; Alleman Hall McCoy Russell & Tuttle LLP

(57) ABSTRACT

Embodiments for diagnosing a humidity sensor are provided. One example method comprises adjusting an engine operating parameter based on humidity of a first gas flow measured by a humidity sensor, and indicating degradation of the humidity sensor if a humidity of a second gas flow measured by the humidity sensor is different than an expected humidity. In this way, degradation of the humidity sensor may be indicated if the humidity of the second gas flow measured by the humidity sensor is different than expected.

8 Claims, 7 Drawing Sheets

(56) References Cited

U.S. PATENT DOCUMENTS

| | | | |
|---|---|---|---|
| 8,881,713 B2* | 11/2014 | Surnilla | F02D 41/0245 123/568.22 |
| 2003/0106304 A1* | 6/2003 | Miyahara | F02D 41/222 60/277 |
| 2007/0181111 A1* | 8/2007 | Cullen | F02D 41/222 123/677 |
| 2009/0254245 A1* | 10/2009 | Bauerle | F02D 41/222 701/29.2 |
| 2012/0227714 A1* | 9/2012 | Surnilla | F02D 41/005 123/568.19 |
| 2014/0298880 A1* | 10/2014 | Pursifull | G01N 33/0006 73/1.06 |
| 2014/0316672 A1* | 10/2014 | Uhrich | F02P 5/045 701/102 |
| 2014/0316676 A1* | 10/2014 | Pursifull | F02P 5/045 701/103 |

OTHER PUBLICATIONS

Jankovic M., et al., "Humidity Sensor Diagnostics," U.S. Appl. No. 13/774,234, filed Feb. 22, 2013, 29 pages.

* cited by examiner

HUMIDITY SENSOR DIAGNOSTICS

FIELD

The present disclosure relates to humidity sensor diagnostics.

BACKGROUND AND SUMMARY

Engine systems may be configured with exhaust gas recirculation (EGR) systems via which at least a portion of the exhaust gas is recirculated to the engine intake. Various sensors may be coupled in the engine system to estimate the amount of EGR being delivered to the engine. These may include, for example, various temperature, pressure, oxygen, and humidity sensors. Since the accuracy of the EGR estimation relies on the correct functioning of the various sensors, periodic sensor diagnostics are used. Further, engines with or without EGR need an estimate of air dilution to optimally set the ignition timing, among other controls. Combustion air dilution may be determined based on humidity measurements using humidity sensors.

One example approach for diagnosing a humidity sensor is illustrated by Xiao et al. in U.S. Pat. No. 7,715,976. Therein, humidity sensor degradation is determined based on a comparison of an intake humidity estimated by a first humidity sensor in the intake manifold with an exhaust humidity estimated by a second humidity sensor in the exhaust manifold and an ambient humidity estimated by a third humidity sensor located outside of the engine. The sensor readings are compared during conditions when all the sensor readings are expected to be substantially equal, such as during engine non-fueling conditions in which the EGR valve is closed. If the readings of the three humidity sensors differ by more than a threshold, humidity sensor degradation may be determined.

However, the inventors herein have identified a potential issue with such an approach. The accuracy of determining degradation of any one humidity sensor may depend on the proper functioning of the other humidity sensors. Further, multiple humidity sensors may not be needed for engine control, and thus additional humidity sensors may not be available for comparison.

Accordingly, embodiments for diagnosing a humidity sensor are provided. One example method comprises adjusting an engine operating parameter based on humidity of a first gas flow measured by a humidity sensor, and indicating degradation of the humidity sensor if a humidity of a second gas flow measured by the humidity sensor is different than an expected humidity.

In this way, degradation of the humidity sensor may be indicated based on the response of the humidity sensor to a second gas flow having a known humidity. During some conditions, the humidity sensor output may be used to adjust engine operating parameters. The humidity sensor may measure the humidity of a first gas flow, such as intake air, during these conditions. Then, under other conditions, the sensor may be exposed to the second gas flow. The second gas flow may be a gas flow having a known humidity, or it may be gas flow that, while the humidity of the gas flow is not precisely known, is known to have a significantly different humidity than the first gas flow, at least under some conditions. The second gas flow may include intake manifold air, EGR, exhaust gas, and/or crankcase gas, for example. If the humidity sensor output is different than an expected output when the sensor is exposed to the second gas flow, degradation of the humidity sensor may be indicated.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
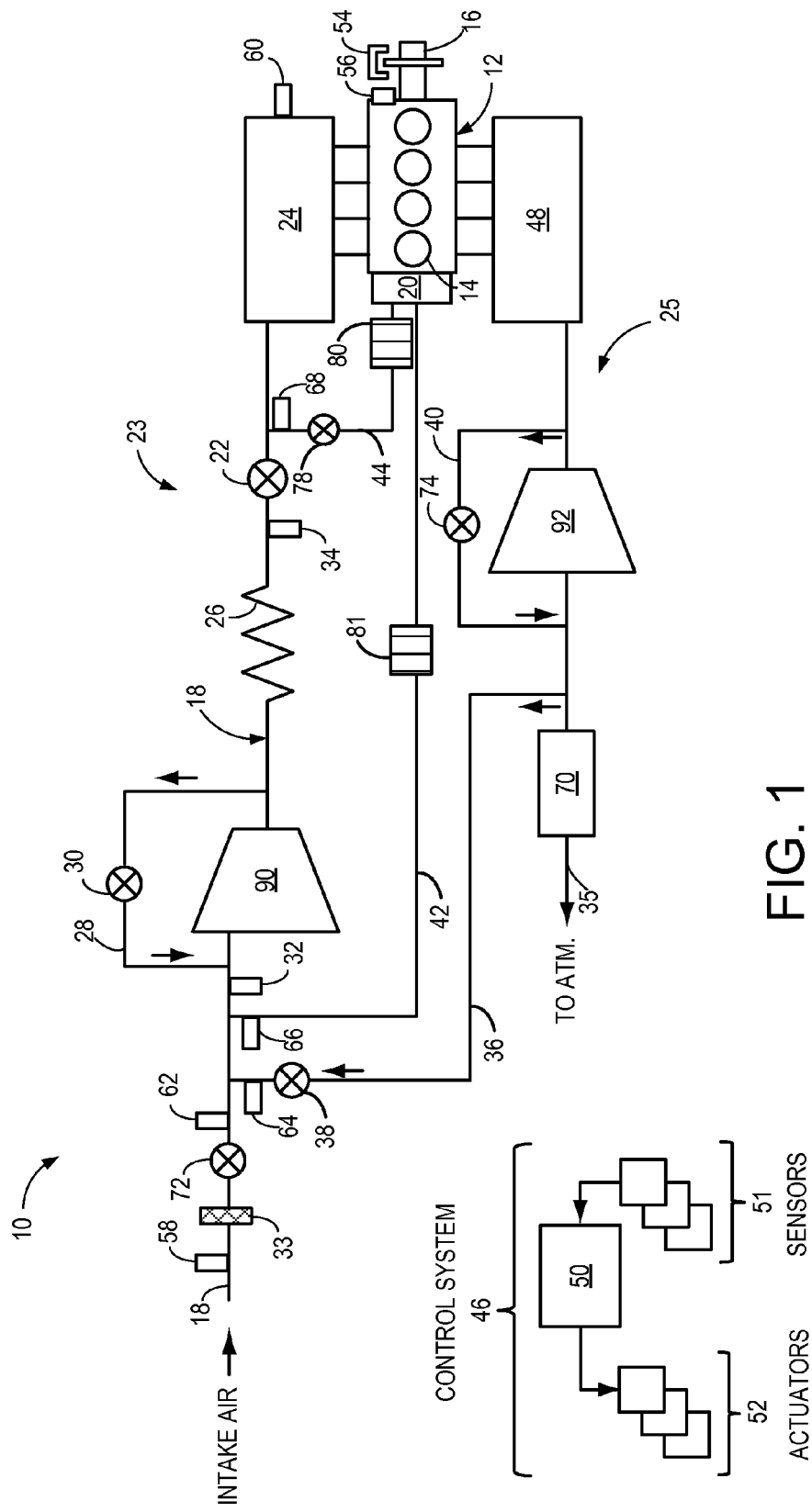
FIG. 1 shows an example engine system including one or more humidity sensors according to a first embodiment of the present disclosure.

FIG. 1 shows an example engine system 10 including an engine 12. In the present example, engine 12 is a spark-ignition engine of a vehicle, the engine including a plurality of cylinders 14, each cylinder including a piston. Combustion events in each cylinder 14 drive the pistons which in turn rotate crankshaft 16, as is well known to those of skill in the art. Crankshaft 16 may be housed in a crankcase 20. Further, engine 12 may include a plurality of engine valves, the valves coupled to the cylinders 14 and controlling the intake and exhaust of gases in the plurality of cylinders 14.

Engine 12 includes an engine intake 23 and an engine exhaust 25. Engine intake 23 includes an engine throttle 22 fluidly coupled to an engine intake manifold 24 along an intake passage 18. Air may enter intake passage 18 from an air intake system (AIS) including an air cleaner 33 in communication with the vehicle's environment and an AIS throttle 72 downstream of air cleaner 33. A position of AIS throttle 72 and/or throttle 22 may be varied by a controller 50 via a signal provided to an electric motor or actuator included with the throttle 22, a configuration that is commonly referred to as electronic throttle control (ETC). In this manner, the throttle 22 may be operated to vary the intake air provided to the intake manifold and the plurality of cylinders 14. The intake 23 may include a mass air flow sensor 58 (in intake passage 18) and a manifold air pressure sensor 60 (in intake manifold 24) for providing respective signals MAF and MAP to the controller 50.

Engine exhaust 25 includes an exhaust manifold 48 leading to an exhaust passage 35 that routes exhaust gas to the atmosphere. Engine exhaust 25 may include one or more emission control devices 70 mounted in a close-coupled position. The one or more emission control devices may include a three-way catalyst, lean NOx trap, diesel particulate filter, oxidation catalyst, etc. It will be appreciated that other components may be included in the engine such as a variety of valves and sensors, as further elaborated in herein.

In some embodiments, engine system 10 is a boosted engine system, where the engine system further includes a boosting device. In the present example, intake passage 18 includes a compressor 90 for boosting an intake aircharge received along intake passage 18. A charge air cooler 26 (or intercooler) is coupled downstream of compressor 90 for cooling the boosted aircharge before delivery to the intake manifold. In embodiments where the boosting device is a turbocharger, compressor 90 may be coupled to, and driven by, a turbine 92 in the engine exhaust 25 of engine system 10. Further compressor 90 may be, at least in part, driven by an electric motor or crankshaft 16.

An optional bypass passage 28 may be coupled across compressor 90 so as to divert at least a portion of intake air compressed by compressor 90 back upstream of the compressor. An amount of air diverted through bypass passage 28 may be controlled by opening compressor bypass valve (CBV) 30 located in bypass passage 28. By controlling CBV 30, and varying an amount of air diverted through the bypass passage 28, a boost pressure provided downstream of the compressor can be regulated. This enables boost control and surge control.

Similarly, an optional bypass passage 40 may be coupled across turbine 92 so to divert at least a portion of exhaust around turbine 92, thus controlling turbine speed and hence boost pressure provided to the engine. The amount of exhaust diverted around turbine 92 may be controlled by opening a wastegate 50 located in bypass passage 40.

In some embodiments, engine system 10 may include an exhaust gas (EGR) recirculation system. In the depicted example, engine system 10 may include a low-pressure EGR (LP-EGR) passage 36 for recirculating at least some exhaust gas from the exhaust passage 35, downstream of the turbine 92, to the intake passage 18, upstream of the compressor 90. LP-EGR passage 36 may include an LP-EGR valve 38 for controlling an EGR flow (i.e., an amount of exhaust gas recirculated) through the passage, as well as an EGR cooler (not shown) for lowering a temperature of exhaust gas flowing through the EGR passage before recirculation into the engine intake. While not shown in FIG. 1, the EGR system may additionally or alternatively include a high-pressure EGR (HP-EGR) passage to recirculate exhaust gas from upstream of turbine 92 to the intake passage 18 downstream of compressor 90.

In the example of FIG. 1 a positive crankcase ventilation system (PCV) is coupled to the engine intake so that gasses in the crankcase may be vented in a controlled manner from the crankcase. During non-boosted conditions (when manifold pressure (MAP) is less than barometric pressure (BP)), the crankcase ventilation system draws air into crankcase 20 via a breather or vent tube 42. Crankcase ventilation tube 42 may be coupled to fresh air intake passage 18 upstream of compressor 90. In some examples, the crankcase ventilation tube 42 may be coupled downstream of air cleaner 33 (as shown). In other examples, crankcase ventilation tube 42 may be coupled to intake passage 18 upstream of air cleaner 33.

The crankcase ventilation system also vents gases out of the crankcase and into intake manifold 24 via conduit 44 (herein also referred to as PCV line 44) which, in some examples, may include a one-way PCV valve 78 (that is, a passive valve that tends to seal when flow is in the opposite direction) to provide continual evacuation of crankcase gases from inside the crankcase 20 before connecting to the intake manifold 24. However, in other examples conduit 44 may not include a one-way PCV valve. In still other examples, the PCV valve may be an electronically controlled valve that is controlled by controller 50.

The crankcase gases may include blow-by of combustion gases from the combustion chamber to the crankcase. PCV line 44 may include an oil separator 80 which filters oil from vapors exiting crankcase 20 before they re-enter the intake manifold 24. Another oil separator 81 may be disposed in crankcase ventilation tube 42 to remove oil from the stream of gasses exiting the crankcases during boosted operation. As such, the gases in the crankcase consist of un-burned fuel, un-combusted air, and fully or partially combusted gasses. Further, lubricant mist is also present. The various oil separators 80, 81 are intended to reduce exiting of the oil mist from the crankcase through the crankcase ventilation system.

Based on engine operating conditions gas flow in conduit 44 may go in both directions, from crankcase 20 towards intake manifold 24 and/or from intake manifold 24 towards crankcase 20. Likewise, gas may flow through breather tube 42 in both directions, from crankcase 20 towards intake passage 18 and/or from intake passage 18 towards crankcase 20. For example, during non-boosted conditions where MAP is lower than Compressor Inlet Pressure (CIP), crankcase gases may flow through conduit 44 from crankcase 20 to intake manifold 24, while air flows through breather tube 42 from intake passage 18 to crankcase 20. In comparison, during boosted engine operation (when MAP is higher than CIP), air may flow through conduit 44 from intake manifold 24 to crankcase 20, and crankcase vapors may flow through breather tube 42 from crankcase 20 to intake passage 18. However, in embodiments where conduit 44 includes a controllable PCV valve, the valve may only allow flow in one direction (that is, of crankcase gases from the crankcase 20 to the intake manifold 24) and disallow flow in the opposite direction (that is, of air from the intake manifold 24 to the crankcase 20). If valve 78 disallows flow from the intake manifold to the crankcase, the crankcase ventilation system is a stale air system at that point. If a small flow of air is allowed to pass from a booster intake manifold to the crankcase, then the system is once again a positive crankcase ventilation system, albeit in the opposite flow direction from non-boosted conditions.

It will be appreciated that, as used herein, PCV flow refers to the flow of gases through the PCV line. This flow of gases may include a flow of intake air only, a flow of crankcase gases only, and/or a flow of a mixture of air and crankcase gases, the composition of the flow based at least on the direction of the flow as well as MAP conditions relative to CIP at the time of flow.

As an example, while the engine is running under light load and moderate throttle opening, the intake manifold's air pressure may be less than crankcase air pressure. The lower pressure of the intake manifold draws fresh air towards it, pulling air from the intake passage 18 via crankcase vent tube 42, then through the crankcase (where it dilutes and mixes with combustion gases), through the PCV valve 78 in conduit 44, and into the intake manifold 24. As another example, when the engine is running boosted at high loads and larger throttle opening, the intake manifold's air pressure may be more than crankcase air pressure. The higher pressure of the intake manifold pushes fresh air towards conduit 44 then through the crankcase (where it dilutes and mixes with combustion gases) and conduit 42 into intake passage 18.

Figure 5:
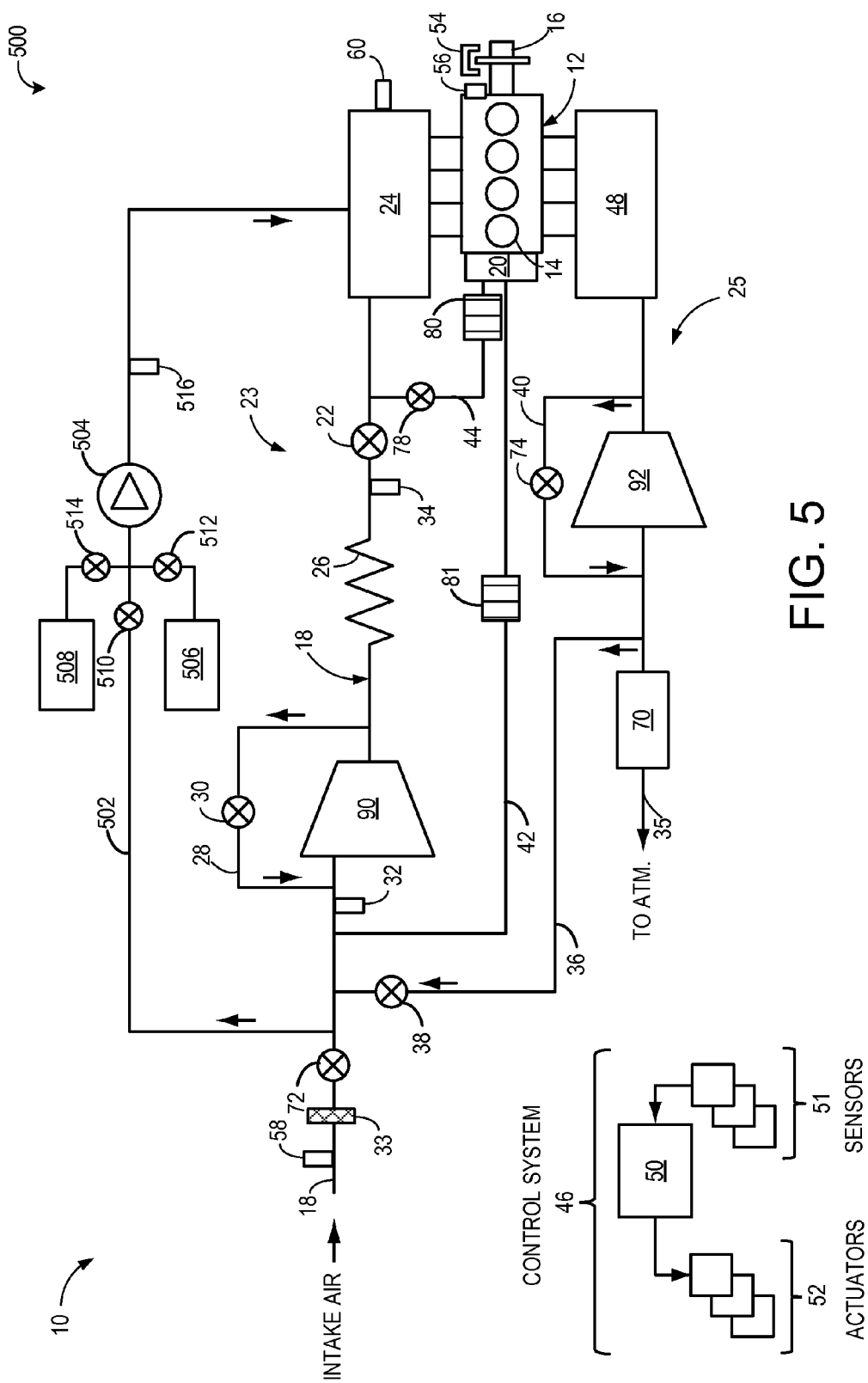
FIG. 5 shows an example engine system including a humidity sensor according to a third embodiment of the present disclosure.

Engine system 10 may also include a control system 46 including a controller 50, sensors 51 and actuators 52. Example sensors include engine speed sensor 54, engine coolant temperature sensor 56, a mass air flow sensor 58, manifold air pressure sensor 60, compressor inlet pressure sensor 32, throttle inlet pressure sensor 34, and barometric pressure (BP) sensor 57. Example actuators include CBV 30, throttle 22, and engine valves, fuel injectors, and other components not illustrated in FIG. 1. Controller 50 may further include a physical memory with instructions, programs and/or code for operating the engine. Example routines executed by controller 50 are shown at FIGS. 5 and 8.

Additionally, one or more humidity sensors may be provided in engine system 10. The humidity sensors may be positioned to determine the humidity of intake air flowing through intake passage 18 during certain conditions and determine the humidity of a different air flow having a known or different humidity during other conditions. If in passage 18, the humidity sensor "sees" or is able to detect both EGR and PCV which are both humid gases. Example positions for the humidity sensor illustrated in FIG. 1 include a first humidity sensor 62 positioned in the intake passage 18 downstream of the AIS throttle 72, a second humidity sensor 64 positioned in the EGR passage 36 downstream of EGR valve 38, a third humidity sensor 66 positioned in crankcase ventilation tube 42, and a fourth humidity sensor 68 positioned in the PCV line 44, downstream of PCV valve 78. In some examples, each humidity sensor may measure the relative humidity and temperature of the gas that the sensor is exposed to. Based on the relative humidity and temperature, the specific humidity of the gas may be determined (e.g., the amount of water per unit mass of gas flow). To measure the relative humidity, a dew point sensor (using a chilled mirror, for example) or a wet bulb/dry bulb sensor may be used. In other examples, the absolute humidity may be measured by a capacitance sensor, and the temperature and/or pressure of the air estimated or measured in order to calculate the relative and/or specific humidity.

In particular, engine control systems tend to want to know the specific humidity, e.g., the humidity ratio, of the air. In other words, the engine control system wants to know how much of the combustion humid air is water vapor (or some other diluent). Some engine humidity sensors measure the absolute humidity, e.g., the mass of water in a volume of air. In many cases, the sensor measures absolute humidity, converts it to relative humidity via selected measurements and assumptions, sends the relative humidity data to the PCM, reconverts to absolute humidity, and then converts to specific humidity. To make these conversions, both pressure and temperature at the point of measurement are measured or inferred. When the humidity sensor is located somewhere other than at barometric pressure, these distinctions have increased importance.

The humidity sensed by first humidity sensor 62 may depend on the position of AIS throttle 72. Humidity sensor location 62 sees neither crankcase ventilation gasses nor EGR gasses. For example, when throttle 72 is open (e.g., no throttling), the humidity at the humidity sensor 62 may be equal to the atmosphere's absolute humidity. When throttle 72 is partially or fully closed (e.g., throttled), the pressure of the intake air at the humidity sensor decreases, and the humidity decreases as a result. Thus, when the AIS throttle is closed, the humidity at the sensor 62 may be equal to the product of atmospheric humidity and change in pressure over pressure. Lowering the total pressure of the gas has zero effect on the specific humidity but does affect the absolute humidity proportionally. Thus, if the total pressure is reduced 20%, the absolute humidity is reduced 20%. By way of example, if the air is throttled from 100 kPa to 80 kPa, the absolute humidity would drop from 0.010 to 0.008 (expressed as a fraction of unity). Thus, if an absolute humidity sensor is employed (regardless of what it may be converted to before it is transmitted), this forms a very strong sensor diagnostic in the presence of slowly changing atmospheric humidity.

The humidity sensed by second humidity sensor 64 may depend on the position of EGR valve 38. When EGR is enabled and EGR valve 38 is at least partially open, the relative humidity of the air flowing in EGR passage 36 past humidity sensor 64 may be at or near 100%, as EGR is comprised of exhaust gas at high temperature, which has a high humidity. However, when EGR valve 38 is closed (when EGR is disabled, such as during idle engine conditions), the relative humidity of the air flowing past sensor 64 may be equal to atmospheric humidity, as the sensor is positioned at the outlet of the EGR passage 36 and thus may be exposed to intake air when EGR is disabled. When the EGR is cooled, condensation may remove much of the humidity, but if not reheated, its relative humidity still tends toward 100% relative humidity. Thus, a humidity sensor positioned at 64 forms both a diagnostic for EGR valve 38 and a diagnostic for a humidity sensor. Compared to many atmospheric air conditions (less than 100% relative humidity), circulated exhaust gas is far more humid than atmospheric air. Thus all measures of humidity increase in the presence of humid exhaust (specific, relative, and absolute).

The humidity sensed by third humidity sensor 66 and/or fourth humidity sensor 68 may depend on boost pressure and EGR valve position. Boost pressure is the manifold absolute pressure (MAP) relative to compressor inlet pressure (CIP). During boosted conditions, when exhaust gas drives turbine 92 and compressor 90 compresses intake air, MAP may be greater than BP and greater than CIP. During non-boosted conditions, MAP may be less than CIP. When MAP is greater than CIP (e.g., during boosted conditions), crankcase gasses may comprise the gas flow flowing past the third humidity sensor 66, and thus the relative humidity of the air flowing past third humidity sensor 66 may be relatively high, such as equal to 100% relative humidity (RH). Also during boosted conditions, the relative humidity of the air flowing past fourth humidity sensor 68 may be equal to atmospheric humidity plus the humidity of EGR, crankcase ventilation, and, in some embodiments, fuel vapor purge (from a fuel vapor canister purge line, for example, not shown in FIG. 1), and thus may also be somewhat above atmospheric humidity. When MAP is less than CIP (e.g., non-boosted conditions), the humidity of air flowing past third humidity sensor 66 may be equal to atmospheric humidity, and the humidity of air flowing past fourth humidity sensor 68 may be equal to the humidity of the crankcase gases and the ventilation air (passing through crankcase 20 prior to reaching conduit 44).

Thus, humidity sensor degradation may be determined if the output of the humidity sensor does not change, or does not change by an expected amount, when the composition of the gas flowing past the humidity sensor changes. For example, referring to second humidity sensor 64, if EGR is initially disabled following engine start-up (during engine idle conditions, for example), the output of the second humidity sensor 64 is expected to indicate atmospheric humidity. Then, when EGR is enabled during subsequent engine operation, the output of the humidity sensor is expected to increase to above that of atmospheric humidity. When the EGR switches from disabled to enabled, degradation may be indicated if the output of the humidity sensor does not change, or if it changes by less than an expected amount. Following indication of a degraded humidity sensor, a vehicle operator may be notified (by lighting a malfunction indicator lamp, for example), a diagnostic code may be set, and/or engine operating parameters may be adjusted.

Figure 2:
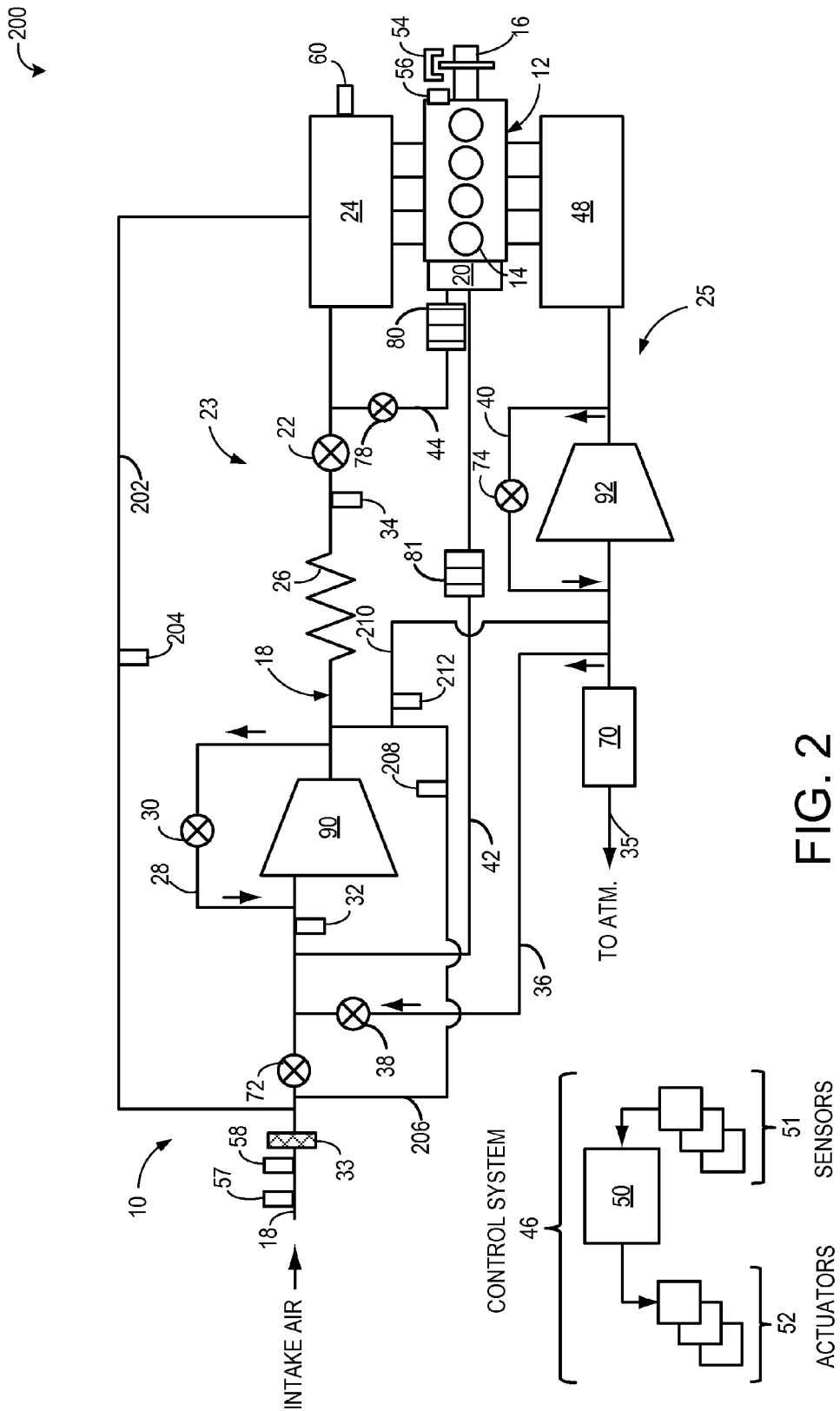
FIG. 2 shows an example engine system including one or more humidity sensors according to a second embodiment of the present disclosure.

FIG. 1 illustrates one or more humidity sensors positioned in existing engine conduits that receive air of differing humidity depending on operating conditions. However, in some embodiments, the one or more humidity sensors may be positioned in specific conduits designed to receive intake air under certain conditions, and receive air of a known and/or different humidity under other conditions. FIG. 2 illustrates an engine system 200 having one or more humidity sensors positioned to receive air having different humidity depending on operating conditions. Engine system 200 includes similar components as the engine system depicted in FIG. 1, and thus reference is made to FIG. 1 for description of like-numbered parts.

A first humidity conduit 202 of FIG. 2 fluidically couples the intake manifold 24 to the intake passage 18 upstream of AIS throttle 72. A fifth humidity sensor 204 is positioned within first humidity conduit 202. During non-boosted engine conditions, intake air from downstream of the filter 33 and upstream of the AIS throttle 72 flows through conduit 202 and past humidity sensor 204. During boosted conditions, air from the intake manifold 24 flows through conduit 202 and past humidity sensor 204. The intake manifold air may include EGR and/or crankcase gas from the PCV system, which may increase the humidity of the intake air. Thus, if the EGR level and fuel composition are known, the humidity of the intake manifold air may be estimated. If the humidity sensor outputs a humidity measurement that is different than the estimated humidity, the humidity sensor may be degraded. Conduit 204 may also contain an open/close valve and an ejector to create vacuum. This vacuum may be used to draw in air samples from an HVAC system (dry air) or through a windshield washer bottle (moist air) or from the exhaust (moist gas).

One or more humidity sensors may be positioned in other locations in the engine system. As shown in FIG. 2, a second humidity conduit 206 fluidically couples the intake passage 18 upstream of AIS throttle 72 to the intake passage 18 downstream of the compressor 90. The second humidity conduit 206 includes a sixth humidity sensor 208. During non-boosted conditions, intake air from upstream the AIS throttle 72 flows through conduit 206 and past humidity sensor 208. During boosted conditions, compressed intake air from downstream of the compressor 90 flows through conduit 206 and past humidity sensor 208. The compressed air may include EGR, and thus the humidity of the compressed air may be estimated based on the known EGR level. If the humidity sensor 208 outputs a humidity measurement that is different than the estimated humidity, degradation of the humidity sensor may be indicated. Conduit 208 may also contain an open/close valve and an ejector to create vacuum. This vacuum may be used to draw in air samples from an HVAC system (dry air) or through a windshield washer bottle (moist air) or from the exhaust (moist gas).

A third humidity conduit 210 fluidically couples the exhaust passage 35 downstream of turbine 92 to the intake passage 18 downstream of the compressor 90 and includes a seventh humidity sensor 212. During non-boosted conditions, exhaust gas expelled from the engine may flow through the conduit 210 and past the humidity sensor 212. During boosted conditions, compressed air from downstream the compressor 90 may flow through the conduit 210 and past the humidity sensor. The exhaust gas may be of a higher humidity than the compressed intake air, and thus humidity sensor degradation may be indicated if the output of the humidity sensor 212 does not increase when the engine shifts from non-boosted to boosted engine conditions.

Thus, the engine system 200 illustrated in FIG. 2 includes one or more humidity sensors that may detect the humidity of a first air source (e.g., filtered intake air) under a first condition (such as non-boosted conditions) and detect the humidity of a second, different air source (e.g., intake manifold air) under a second condition (such as boosted conditions). The humidity of the second air source may be known or substantially different than the first air source, such that deviation of the humidity sensor output from a known or expected humidity may be indicative of humidity sensor degradation.

Figure 3:
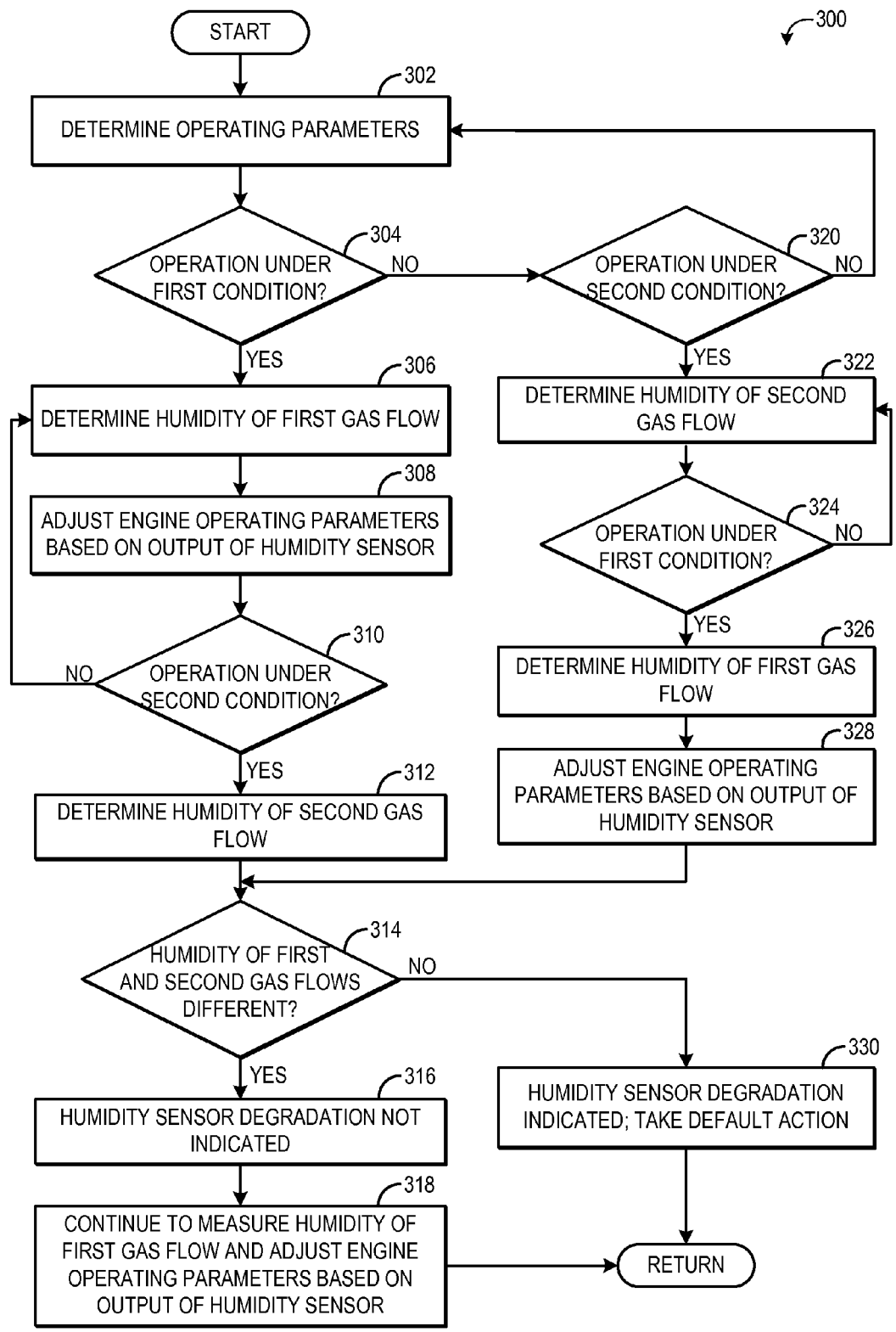
FIG. 3 is a flow chart illustrating a method for testing a humidity sensor according to an embodiment of the present disclosure.

Turning now to FIG. 3, a method 300 for testing a humidity sensor is depicted. Method 300 may be carried out by an engine controller, such as controller 50 of FIGS. 1 and 2, according to instructions stored thereon. Method 300 may determine if a humidity sensor (such as one of the humidity sensors depicted in FIGS. 1 and 2) is degraded based on the output of the humidity sensor during conditions where the humidity of the air flowing past the humidity sensor is known, or is known to be different than the humidity of the intake air that the humidity sensor is configured to measure.

At 302, method 300 includes determining engine operating parameters. The engine operating parameters may include engine speed and load, EGR valve position and/or the amount of EGR flowing to the engine, boost pressure, MAP, etc. At 304, it is determined if the engine is operating under a first condition. The first condition may include non-boosted engine conditions, wherein the MAP is less than barometric pressure (e.g., MAP<CIP). In another example, the first condition may include EGR being disabled. During the first condition, a first gas flow flows past the humidity sensor. In some examples, the first gas flow may include air from an intake air system. This air may be similar to ambient air, in that it may be free of exhaust or other gas sources. If the engine is not operating under the first condition, method 300 proceeds to 320, which will be explained in more detail below. If the engine is operating under the first condition, at 306, the humidity of the first gas flow is determined based on the output from the humidity sensor. At 308, one or more engine operating parameters is adjusted based on the output of the humidity sensor. For example, the amount of EGR that is directed to the engine may be adjusted based on the humidity of the intake air as determined by the humidity sensor. A desired amount of EGR may be determined based on operating conditions, such as engine speed and load. The actual amount of delivered EGR may be measured based on the EGR valve position, feedback from an intake and/or exhaust oxygen sensor, and other parameters. The EGR valve may be adjusted if the actual delivered amount of EGR is not equal to the desired EGR. Because the humidity of the intake air reduces the combustion stability of the charge air, which is further reduced by the EGR, if the humidity is relatively high, the amount of delivered EGR may be reduced. Other operating parameters that may be adjusted based on humidity of the intake air include spark timing, air-fuel ratio, and other parameters.

At 310, it is determined if the engine is operating under the second condition. The second condition may include boosted engine operation, where MAP is greater than BP. In another example, the second condition may include EGR being enabled. During the second condition, a second gas flow may be directed past the humidity sensor. The second gas flow may be a different gas flow than the first gas flow, and/or may be the same gas flow directed in an opposite direction of the first gas flow. The second gas flow may have a known or estimated humidity, or the second gas flow may have a humidity that is substantially different than the humidity of the first gas flow. For example, the first gas flow may be filtered intake air, and the second gas flow may be air from the intake manifold that includes EGR and crankcase gasses.

If the engine is not operating under the second condition, method 300 loops back to 306 to continue to determine the humidity of the first gas flow and adjust engine operating parameters based on the humidity of the first gas flow. However, if the engine is operating under the second condition, method 300 proceeds to 312 to determine the humidity of the second gas flow based on output from the humidity sensor. At 314, method 300 determines if the humidity of the first gas flow is different than the humidity of the second gas flow. As used herein "different than" may include a difference of more than a threshold amount, such as 10%. That is, even if the humidity of the first and second gas flows are not equal, they may be considered to the same (or not different than each other) if they differ by less than the threshold amount.

If the humidity of the first gas flow is different than the humidity of the second gas flow, method 300 proceeds to 316 to indicate no humidity sensor degradation. As explained previously, the second gas flow may have a substantially different humidity than the first gas flow. For example, the first gas flow may include only filtered intake air that is mostly ambient air free from exhaust or other combustion products. The second gas flow may include exhaust gas in the form of EGR, crankcase gas from the PCV system, and/or exhaust from upstream of downstream the turbine, as well as intake air in some conditions. As such, the second gas flow may be of higher humidity than the second gas flow. When the humidity sensor is functional, it will detect that the humidity has changed when the engine switches from flowing the first gas flow by the humidity sensor to flowing the second gas flow by the humidity sensor. Thus, no degradation is indicated when the humidity sensor detects a change in humidity responsive to the engine operating under the second condition. In some examples, the humidity of the second gas flow may be known, and degradation of the humidity sensor may be determined if the output from the humidity sensor is different than the known humidity.

Because the humidity sensor is not degraded, method 300 continues to measure the humidity of the first gas flow (when the engine is operating under the first condition) and adjust the engine operating parameters based on the humidity of the first gas flow at 318. Method 300 then returns.

If the humidity of the first gas flow is not different than the humidity of the second gas flow at 314, method 300 proceeds to 330 to indicate humidity sensor degradation and take default action. As the humidity of the second gas flow is different than (e.g., greater than) the humidity of the first gas flow, if the humidity sensor output does not change (or does not change by a large enough amount), the humidity sensor may be "stuck" in place and not giving an accurate measurement of the humidity. Degradation of the humidity sensor may also be indicated if the humidity of the second gas flow as measured by the humidity sensor is different than the known or expected humidity of the second gas flow. Further, in some conditions the actual humidity of the first gas flow may be the same as the humidity of the second gas flow. For example, if it is raining, the relative humidity of the first gas flow (e.g., intake air) may be 100%, which may be equal to the humidity of the second gas flow. In such cases, degradation of the humidity sensor may not be indicated if the humidity sensor output indicates the humidity of the first and second gas flows are equal. Rather, if the controller detects the ambient humidity to be 100% (based on activation of the windshield wipers, for example), it may delay the humidity sensor test until the humidity sensor is measuring a relative humidity lower than 100%.

The default action taken in response to degradation of the humidity sensor may include notifying a vehicle operating that the sensor is degraded (by lighting a malfunction indicator light and/or setting a diagnostic code, for example). Further, one or more operating parameters may be adjusted, such as the amount of EGR directed to the engine. Without an accurate determination of the humidity of the intake air, the relative humidity may be assumed to be 100% (which the PCM would convert to a specific humidity for purposes of computing its contribution to dilution), resulting in reduced EGR levels. Method 300 then returns.

Returning to 304 of method 300, if it is determined that the engine is not currently operating under the first condition, method 300 proceeds to 320 to determine if the engine is operating under the second condition. The second condition may include boosted operation, as explained previously, or other condition that results in the second gas flow being directed past the humidity sensor. If the engine is not operating under the second condition, method 300 proceeds back to 302 to continue to monitor engine operating parameters. If the engine is operating under the second condition, method 300 proceeds to 322 to determine the humidity of the second gas flow. At 324, it is determined if the engine is now operating under the first condition. If not, method 300 loops back to 324 to continue to determine the humidity of the second gas flow. If the engine is now operating under the first condition (e.g., if the engine has switched from operating under boosted to non-boosted conditions), method 300 proceeds to 326 to determine the humidity of the first gas flow, and at 328, adjust one or more operating parameters based on the humidity of the first gas flow. Method 300 then proceeds to 314 to compare the humidity of the first gas flow to the humidity of the second gas flow, and indicate degradation of the sensor based on the difference between the two measured humidities, as explained previously.

Figure 4:
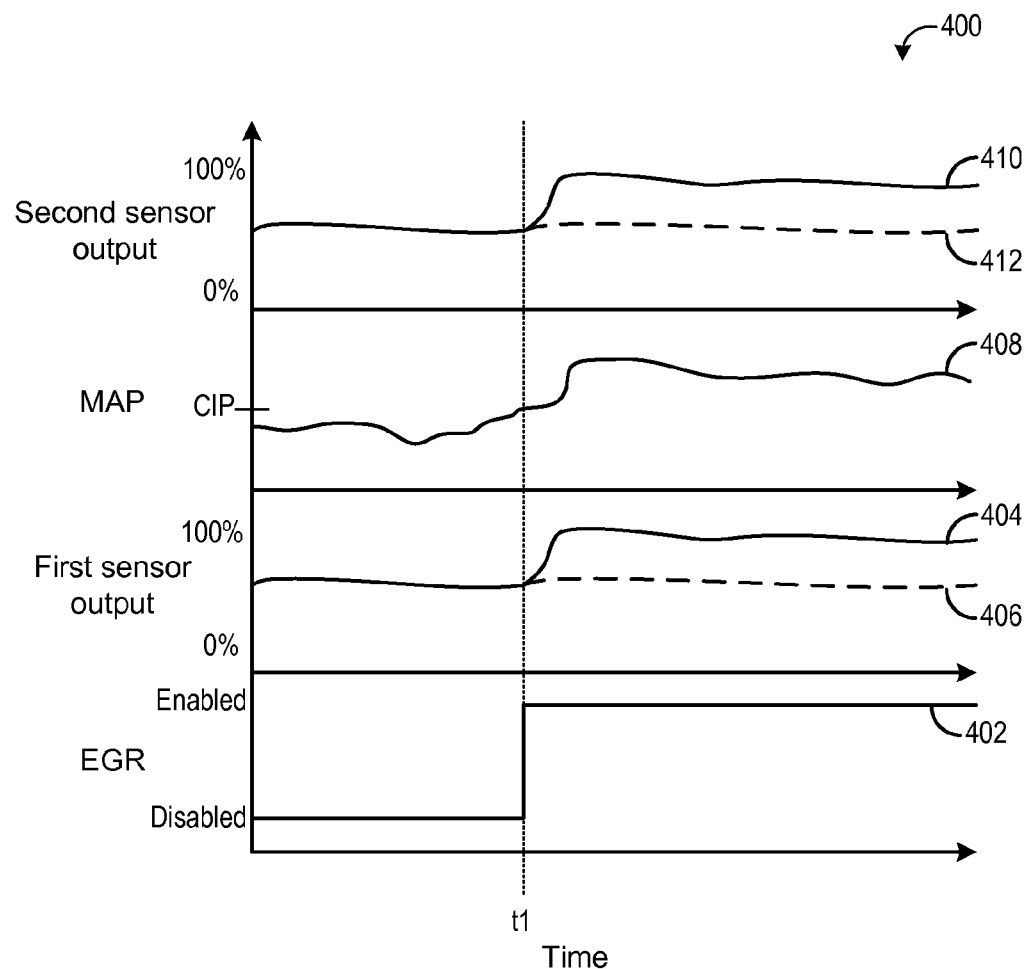
FIG. 4 is a diagram illustrating parameters of interest during execution of the method of FIG. 3.

FIG. 4 is a diagram 400 illustrating example parameters of interest during a humidity sensor test as carried out according to the method of FIG. 3. In the example shown in FIG. 4, a first humidity sensor positioned at an outlet of an EGR passage (e.g., humidity sensor 64 of FIG. 1) is being tested as well as a second humidity sensor positioned in a conduit coupled to the intake upstream of an AIS throttle and to the intake manifold (e.g., humidity sensor 204 of FIG. 2). For each parameter illustrated in FIG. 4, time is depicted along the vertical axis and relative levels of each respective parameter are illustrated along the horizontal axis. Referring first to the EGR status, which is illustrated by curve 402, EGR is disabled prior to time t1. During idle engine operation, for example, EGR may be disabled in order to prevent unstable combustion. Then, following time t1, EGR is enabled. The amount of EGR that is directed to the engine may be based on engine speed and load, and thus following time t1, the engine may begin non-idle operation at a speed/load point in a range to start flowing EGR.

Responsive to the activation of EGR, the humidity measured by the first humidity sensor may change. As shown by curve 404, prior to time t1, the humidity measured by the first humidity sensor is relatively low, such as 50% RH, as the first humidity sensor is measuring the humidity of the filtered intake air. Following time t1, if the first humidity sensor 64 is functional, the humidity determined by the sensor increases to 100%, as the humidity sensor is now measuring the humidity of the EGR. However, if the first humidity sensor is not functional, it may not measure the change in humidity responsive to the activation of EGR, as shown by curve 406, which does not increase responsive to EGR activation.

Referring now to the second humidity sensor 204, it may measure the humidity of the filtered intake air prior to time t1, as before time t1, the MAP is below CIP, as illustrated by curve 408. At time t1, the MAP is greater than CIP. As a result, the gas flowing past the second humidity sensor switches from flowing from the air intake system to the intake manifold, and instead flows from the intake manifold to the air intake system. The air in the intake manifold includes EGR and crankcase gasses from the PCV system under some conditions. Thus, as shown by curve 410, when the second humidity sensor is functional, it measures an increase in humidity following the switch from non-boosted to boosted conditions at time t1. If the sensor is degraded it may continue to indicate that the humidity is the same as the intake air, as illustrated by curve 412.

Thus, the methods and systems described in FIGS. 1-4 provide for a method comprising adjusting an engine operating parameter based on humidity of a first gas flow measured by a humidity sensor, and indicating degradation of the humidity sensor if a humidity of a second gas flow measured by the humidity sensor is different than an expected humidity. The first gas flow may comprise air from an engine air intake system. Adjusting the engine operating parameter may comprise adjusting an amount of exhaust gas recirculated from an engine exhaust to an engine intake.

In an example, the second gas flow comprises air from an engine intake manifold, and the expected humidity is a function of fuel composition and an amount of exhaust gas recirculated from an engine exhaust to the intake manifold. In another example, the second gas flow comprises exhaust gas recirculated from an engine exhaust system, and the expected humidity is at or near maximum humidity. The maximum humidity may be 100% relative humidity in one example. In a further example, the second gas flow comprises crankcase gas from a crankcase vent tube, and the expected humidity is at or near maximum humidity.

In an example, the first gas flow may comprise air from an air intake system, exhaust gas recirculation system, and crankcase ventilation system. The second gas flow may comprise crankcase gas and air from the air intake system, and the expected humidity may be at or near maximum humidity.

In an example, the first gas flow comprises air from an air intake system at a first pressure, the second gas flow comprises air from the air intake system at a second pressure, and the expected humidity is a function of the humidity of the air at the first pressure and a difference between the first pressure and the second pressure.

Another embodiment refers to a system comprising an engine coupled to an intake system and an exhaust system; a humidity sensor; and a controller including instructions to, during a first condition when the humidity sensor is exposed to a first gas flow, adjust an engine operating parameter based output of the humidity sensor; and during a second condition when the humidity sensor is exposed to a second gas flow, indicate degradation of the humidity sensor if output of the humidity sensor is different than an expected output.

In one example of the system, the humidity sensor may be positioned in the engine intake system downstream of air intake system throttle, the first condition may comprise the air intake system throttle being in a fully open position, the first gas flow may comprise intake air at barometric pressure, the second condition may comprise the air intake system throttle being in a closed or partially closed position, and the second gas flow may comprise intake air at less than barometric pressure.

In one example of the system, the humidity sensor is positioned in an exhaust gas recirculation (EGR) passage outlet, the first condition comprises an EGR valve being in a fully closed position, the first gas flow comprises intake air, the second condition comprises the EGR valve being in a partially or fully open position, and the second gas flow comprises exhaust gas.

In another example of the system, the humidity sensor is positioned in a crankcase ventilation system vent tube, the first condition comprises intake manifold pressure less than barometric pressure, the first gas flow comprises intake air, the second condition comprises intake manifold pressure greater than barometric pressure, and the second gas flow comprises crankcase ventilation air.

In a further example of the system, the humidity sensor is positioned in a crankcase ventilation system purge tube, the first condition comprises a positive crankcase ventilation valve being in a fully closed position, the first gas flow comprises intake air, the second condition comprises positive crankcase ventilation valve being in fully or partially open position, and the second gas flow comprises crankcase gases and crankcase ventilation air.

In a still further example of the system, the humidity sensor is positioned in a passage fluidically coupled to an engine intake manifold and to an intake passage upstream of an air intake system throttle, the first condition comprises intake manifold pressure less than barometric pressure, the first gas flow comprises intake air, the second condition comprises intake manifold pressure greater than barometric pressure, and the second gas flow comprises intake air, exhaust gas, and crankcase gas.

In an example of the system, the humidity sensor is positioned in a passage fluidically coupled to an intake passage upstream of an air intake system throttle and the intake passage downstream of a compressor outlet, the first condition comprises intake manifold pressure less than barometric pressure, the first gas flow comprises intake air, the second condition comprises intake manifold pressure greater than barometric pressure, and the second gas flow comprises intake air and exhaust gas.

In an example of the system, the humidity sensor is positioned in a passage fluidically coupled to an intake passage downstream of a compressor outlet and an exhaust passage downstream of a turbine outlet, the first condition comprises intake manifold pressure greater than barometric pressure, the first gas flow comprises intake air and exhaust gas, the second condition comprises intake manifold pressure less than barometric pressure, and the second gas flow comprises exhaust gas.

Another embodiment refers to a method comprising adjusting an engine operating parameter based on humidity of a gas flowing in a first direction; and indicating degradation of the humidity sensor based on the humidity of the gas flowing in a second, opposite direction. Adjusting an engine operating parameter may include adjusting an amount of exhaust gas recirculated to an engine intake.

In a first example, the gas flowing in the first direction may include the gas flowing from an intake passage upstream of an air intake system throttle to an intake manifold, and the gas flowing in the second, opposite direction includes the gas flowing from the intake manifold to the intake passage upstream of the air intake system throttle.

In a second example, the gas flowing in the first direction includes the gas flowing from an intake passage downstream of a compressor outlet to an exhaust passage downstream of a turbine outlet, and the gas flowing in the second, opposite direction includes the gas flowing from the exhaust passage downstream of the turbine outlet to the intake passage downstream of the compressor outlet.

The humidity sensors depicted in FIGS. 1 and 2 may be tested for degradation when the gas flowing past the sensors switches from a first gas flow to a second gas flow having a different humidity than the first gas flow. The switch from the first gas flow to the second gas flow may occur due to a pressure differential resulting from a change in engine operation, for example due to a switch from non-boosted to boosted engine operation. However, in some examples the engine may not operate in boosted or non-boosted conditions long enough to accurately assess the functionality of the humidity sensors.

Thus, as illustrated in FIG. 5 and described in more detail below, the humidity sensor or sensors may be positioned to receive intake air gas flow during a majority of the engine operating cycle, and then during a test cycle initiated by the engine controller, receive gas from a second source that is either of high relative humidity or of low relative humidity. The high or low humidity gas may be pumped from a gas source external to the engine, such as from a windshield wiper fluid chamber or from downstream of an air conditioning evaporator. In this way, the humidity sensor may be purposely exposed to either high humidity or low humidity in order to check that the sensor is functioning.

For example, in order to humidify the air stream, air may be drawn out of the ullage space of the windshield washer bottle. Replacement air comes from atmosphere to the bottom of the washer bottle which effectively functions as a bubbler, commonly used to humidify air streams. For example, the O2 enriched air from an oxygen generator often passes through this sort of bubbler to humidify air for breathing.

FIG. 5 shows another example of an engine system 500. Engine system 500 includes similar components as the engine system depicted in FIG. 1, and thus reference is made to FIG. 1 for description of like-numbered parts. Rather than one or more sensors placed in an existing engine air conduit, as depicted in FIG. 1, engine system 500 of FIG. 5 includes a single humidity sensor 516. Humidity sensor 516 is positioned in a conduit 502 that is fluidically coupled to the intake passage 18 downstream of the AIS throttle 72 at one end and fluidically coupled to the intake manifold 24 or other low-pressure sink at the other end. Also positioned in conduit 502 is a pump 504. Pump 504 may be powered by a motor that is activated in response to a command from the controller, or it may be mechanically driven via the engine. When activated, pump 504 may direct air from an upstream source (such as the intake passage 18) past the humidity sensor 516. Other air sources that may be pumped past humidity sensor 516 include air from a windshield washer fluid chamber 506 (or other fluid-containing chamber) and air from downstream an air conditioning system component 508, such as an evaporator. While not shown in FIG. 5, component 508 may be coupled to other air conditioning system conduits and components. A pump is strictly optional because when a low pressure in the intake manifold exists, a pump is not required to create a flow. In some examples, if a pumping action is desired then a lower cost aspirator, e.g., ejector, may be used in a number of possible configurations. In this case, the aspirator would be located along conduit 502 and valve 510 would control aspirator flow.

To selectively modulate the air source pumped past the humidity sensor 516, one or more valves may be present. A first valve 510 may be positioned in conduit 502 upstream of pump 504 to control the flow of air from the intake passage 18 to the humidity sensor 516. A second valve 512 may be positioned in a conduit coupling the washer fluid chamber 506 to conduit 502. The second valve 512 may control the flow of air from the washer fluid chamber to the humidity sensor 516. A third valve 514 may be positioned in a conduit coupling the air conditioning system component 508 to the conduit 502. The third valve may control the flow of air from the air conditioning component 508 to the humidity sensor 516. If one found the windshield washer bottle method to be costly, the humid exhaust may be sampled instead. The windshield washer humidity may also form a windshield washer low level sensor. If the water level was below the dip tube (the bottle's air inlet tube) little humidification would take place.

Thus, during standard engine operation when a humidity sensor test cycle is disabled, intake air may be directed past humidity sensor 516. The intake air may be pumped via pump 504, or it may be naturally drawn into conduit 502 based on the pressure differential between the intake passage and intake manifold. During these conditions, first valve 510 may be fully or partially open, and second and third valves 512, 514 may be fully closed. When the humidity sensor test cycle is enabled, first valve 510 is closed to block intake air from flowing past the humidity sensor 516 and pump 504 is activated. In some examples, second valve 512 may be opened while third valve 514 is closed in order to pump air from the washer fluid chamber 506 past the humidity sensor 516. In other examples, second valve 512 is closed while third valve 514 is opened in order to pump air from the air conditioning system component 508 past the humidity sensor 516.

Humidity sensor degradation may be indicated if the output of the humidity sensor does not change responsive to the test cycle being enabled. For example, the humidity of the intake air may be relatively equal to ambient humidity, and thus may be around 60% in one example. The humidity of the intake air may remain relatively stable over a long duration of time, and thus it may be difficult to determine if the sensor is accurately measuring humidity. To test the sensor, gas flow having a high humidity, such as near 100% relative humidity, may be purposely pumped past the humidity sensor from the washer fluid chamber. Because the washer fluid chamber includes water that is frequently at a high temperature and/or agitated, the air in the chamber may reach a relatively high humidity. Alternatively, gas flow having a low humidity, such as 20%, may be purposely pumped past the humidity sensor from the air conditioning outlet duct. The process of cooling air via the air conditioning system may remove some or all of the water vapor from the cooled air, and thus air from downstream an air conditioning system component (such as the evaporator) may have a low humidity. Thus, if high or low humidity air is pumped past the humidity sensor but the output of the humidity does not increase or decrease as expected, degradation of the humidity sensor may be indicated.

While FIG. 5 shows the conduit 502 in fluid communication with intake manifold 24, it is possible the conduit 502 may be coupled to other components. For example, the conduit 502 may be open to atmosphere instead. In another example, the conduit 502 may be coupled to the vehicle cabin, or it may be coupled to an air line leading back to the washer fluid chamber 506 or air conditioning component 508. Further, an ejector (not shown) may be positioned in conduit 502 downstream of humidity sensor 516 in order to draw air past the humidity sensor.

Figure 6:
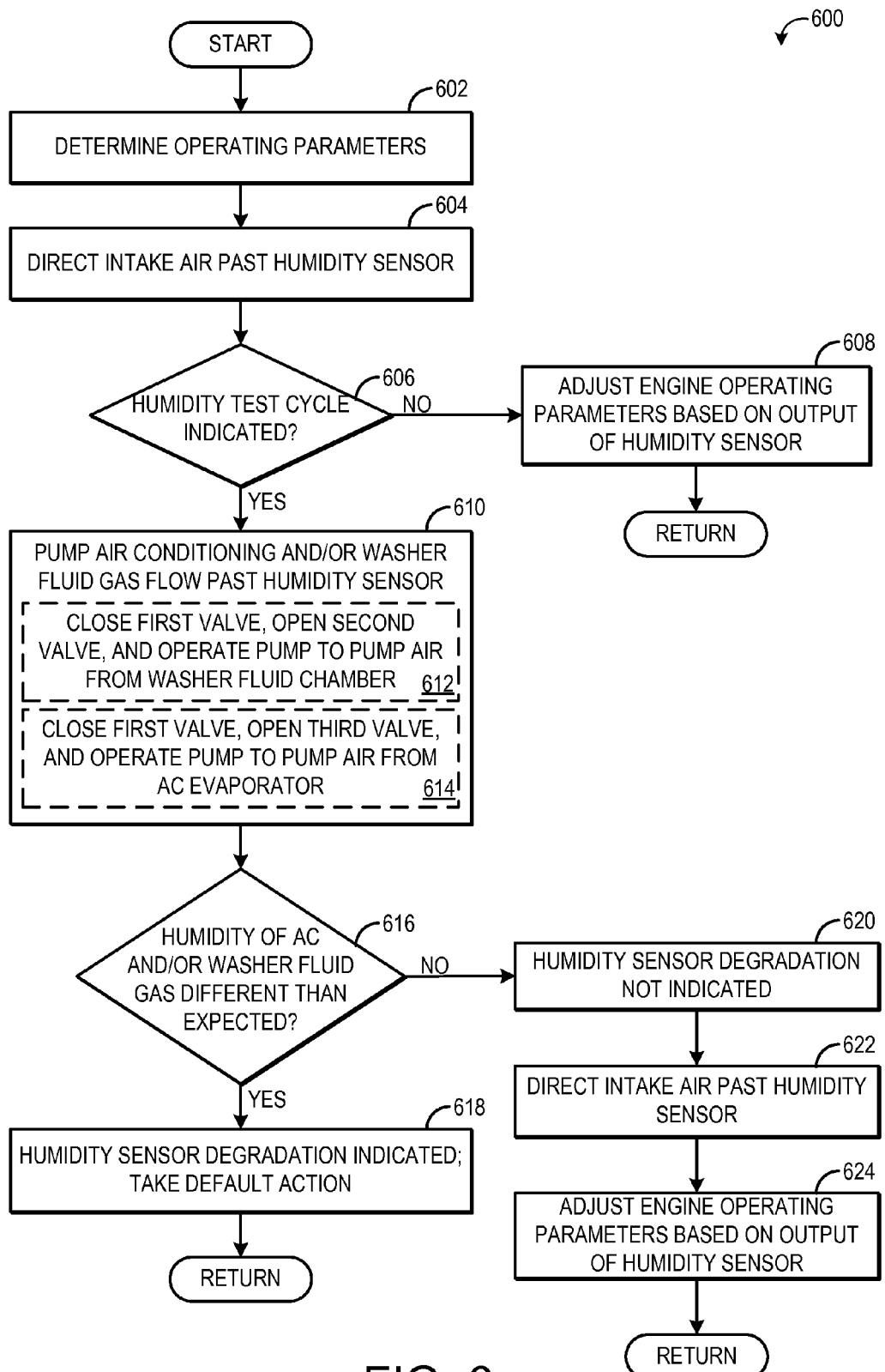
FIG. 6 is a flow chart illustrating a method for testing a humidity sensor according to another embodiment of the present disclosure.

Turning now to FIG. 6, a method 600 for testing a humidity sensor, such as humidity sensor 516 of FIG. 5, is illustrated. Method 600 may be carried out by an engine controller (e.g., controller 50) according to instructions stored thereon. At 602, method 600 includes determining engine operating parameters. The engine operating parameters determined may include, but are not limited to, engine speed and load, time since a previous humidity sensor test cycle was performed, current humidity sensor output, and other parameters. At 604, intake air system air is directed past the humidity sensor, which may include a valve positioned in a conduit coupling the intake passage to the intake manifold and housing the humidity sensor being opened.

At 606, it is determined if a humidity sensor test cycle is indicated. The humidity sensor test cycle may be activated if a threshold amount of time has elapsed since a previous humidity sensor test cycle. For example, the humidity sensor test cycle may be performed once every week, once every 100 miles, or other duration. If the humidity sensor test cycle is not indicated, method 600 proceeds to 608 to adjust one or more engine operating parameters based on the output from the humidity sensor. For example, the amount of EGR directed to the engine may be adjusted based on the humidity of the intake air. Method 600 then returns.

If the humidity sensor test cycle is indicated, method 600 proceeds to 610 to pump air conditioning and/or washer fluid chamber gas past the humidity sensor. This may include, as indicated at 612, closing the first valve and opening the second valve to pump gas from the washer fluid chamber to the humidity sensor. In doing so, gas with high humidity is directed past the humidity sensor. In another example, as indicated at 614, the first valve may be closed and the third valve may be opened to pump air from downstream an air conditioning system component to the humidity sensor. This will expose the humidity sensor to gas having a low humidity.

If the engine system is configured such that both the washer fluid chamber gas flow and the air conditioning system gas flow may be pumped past the humidity sensor, the decision of whether to expose the humidity sensor to the high humidity air or the low humidity air may be based on the humidity of the intake air sensed by the humidity sensor prior to the initiation of the test cycle. For example, if the intake air is at a relatively high humidity, the air from the air conditioning system may be directed past the sensor during the test cycle. Conversely, if the intake air is at a relatively low humidity, the air from the washer fluid chamber may be directed past the sensor during the test cycle. In this way, the humidity sensor may be exposed to a large change in humidity during the test cycle.

At 616, it is determined if the humidity of the air pumped past the humidity sensor during the test cycle is different than expected (e.g., if the humidity of the washer fluid chamber air or the air conditioning air is different than expected), based on the output of the humidity sensor. The humidity of the washer fluid chamber air may be expected to be at or near 100% relative humidity, for example, while the humidity of the air conditioning air may be expected to be below 50% relative humidity. If the humidity of the air pumped past the humidity sensor is different than expected (e.g., if it is more than 10% different than the expected humidity), method 600 proceeds to 618 to indicate humidity sensor degradation and take default action. The default action may include notifying a vehicle operator, setting a diagnostic code, and/or adjusting engine operating parameters to compensate for the degraded humidity sensor. If the humidity of the air pumped past the humidity sensor (as determined by the output of the humidity sensor) is not different than expected, method 600 proceeds 620 to indicate that the humidity sensor is not degraded. At 622, intake air is again directed past the humidity sensor, and at 624, one or more engine operating parameters are adjusted based on the output of the humidity sensor. Method 600 then returns.

Figure 7:
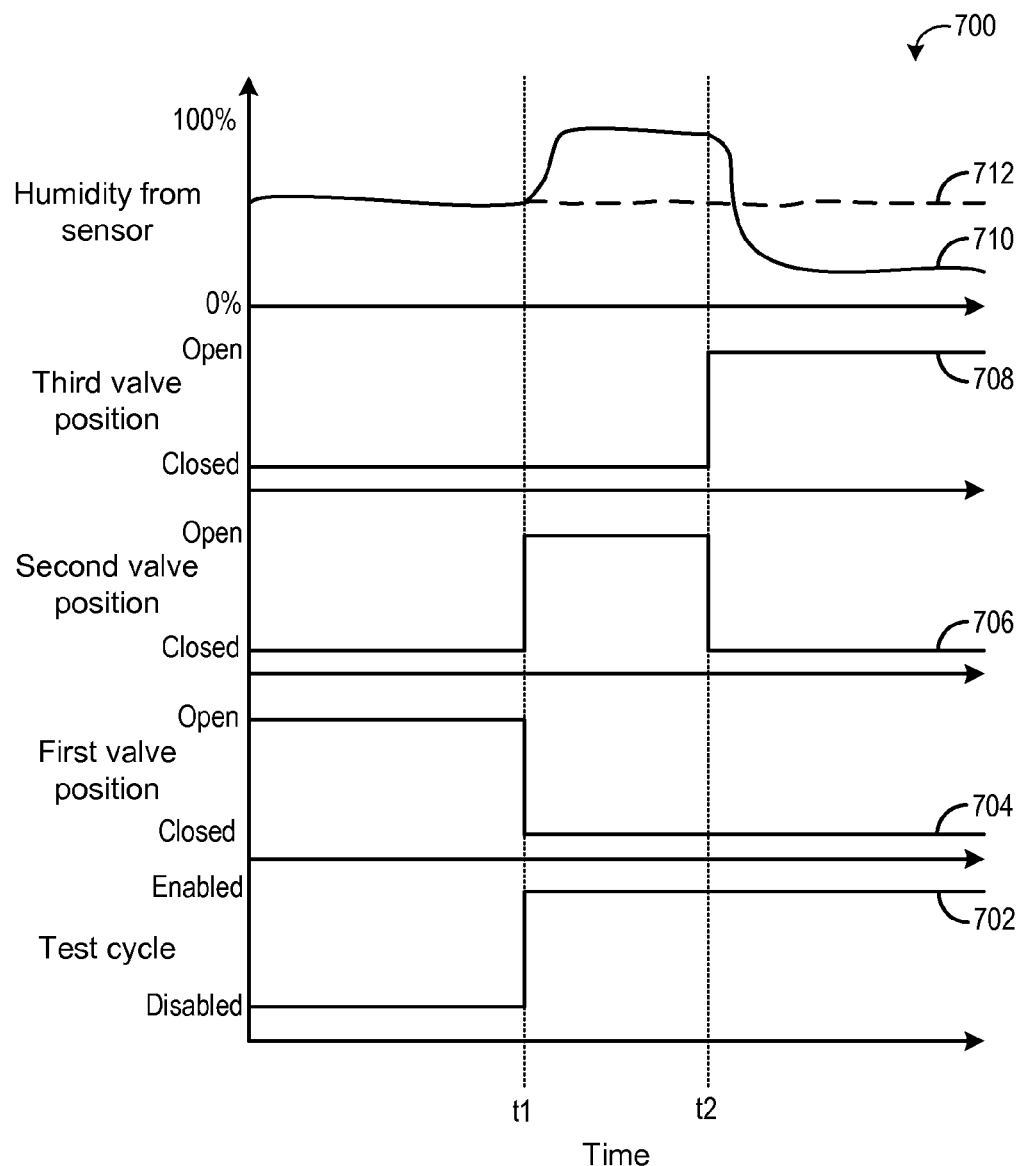
FIG. 7 is a diagram illustrating parameters of interest during execution of the method of FIG. 6.

FIG. 7 is a diagram 700 illustrating example parameters of interest during a humidity sensor test cycle as carried out according to the method of FIG. 6. For each parameter illustrated in FIG. 7, time is depicted along the vertical axis and relative levels of each respective parameter are illustrated along the horizontal axis. Prior to time t1, a humidity sensor test cycle is disabled, as shown by curve 702. Intake air flows past the humidity sensor, due to the first valve being open (as illustrated by curve 704) and the second and third valves being closed (as illustrated by curves 706 and 708, respectively). The humidity measured by the humidity sensor, illustrated by curve 710, is near 60%.

At time t1, the humidity sensor test cycle is enabled. As a result, the first valve is closed. Also, as shown in FIG. 7, the second valve is opened. Thus, air from the washer fluid chamber is pumped past the humidity sensor. Curve 710 shows the response of a functional humidity sensor, which outputs an increased humidity (e.g., 100%) responsive to the washer fluid chamber air being directed past the humidity sensor. However, if the humidity sensor is degraded, as illustrated by dashed curve 712, the humidity as determined by the humidity sensor may not change.

At time t2, the second valve is closed and the third valve is opened. Thus, the air from the air conditioning system is pumped past the humidity sensor (and not the air from the washer fluid chamber). Curve 710 shows that the humidity as measured by the humidity sensor drops in response to the air conditioning air being pumped past the humidity sensor. However, if the humidity sensor is degraded, as shown in by curve 712, it may continue to indicate 60% humidity and not the decrease in humidity due to the low humidity air conditioning air.

Thus, the system and method presented in FIGS. 5-7 provide for a method comprising, responsive to humidity sensor test cycle, pumping air conditioning and windshield washer gas flows past a humidity sensor, and indicating humidity sensor degradation based on a response of the humidity sensor to the air conditioning and windshield washer gas flows. The air conditioning and windshield washer gas flows may each have a known humidity.

Pumping the windshield washer gas flow past the humidity sensor may comprise blocking air flow from an engine air intake system to the humidity sensor and directing air flow from the a chamber housing windshield washer fluid to the humidity sensor. Indicating humidity sensor degradation may further comprise indicating humidity sensor degradation if output from the humidity sensor does not increase when the air flow from the chamber is directed to the humidity sensor.

The method may further comprise if degradation of the humidity sensor is not indicated, directing air flow from the engine air intake system to the humidity sensor and adjusting an engine operating parameter responsive to output from the humidity sensor. Pumping the air conditioning gas flow past the humidity sensor may comprise blocking air flow from an engine air intake system to the humidity sensor and directing air flow from downstream of an air conditioning system evaporator to the humidity sensor. Indicating humidity sensor degradation may further comprise indicating humidity sensor degradation if output from the humidity sensor does not decrease when the air flow from the downstream of the air conditioning system evaporator is directed to the humidity sensor.

An embodiment refers to a system comprising an engine having an air intake system; a humidity sensor; a chamber housing windshield washer fluid; and a pump configured to direct air flow from the air intake system and the chamber to the humidity sensor. The humidity sensor may be positioned in a passage fluidically coupled to the pump, and the system may further comprise a first valve configured to selectively supply air from the air intake system to the pump and a second valve configured to selectively supply air from the chamber to the pump.

The system may further comprise a controller including instructions to close the first valve and open the second valve and operate the pump to direct air from the chamber to the humidity sensor. The controller may include instructions to indicate degradation of the humidity sensor if humidity measured by the humidity sensor does not increase responsive to the air from the chamber being directed to the humidity sensor. The controller may include further instructions to, if degradation of the humidity sensor is not indicated, open the first valve and close the second valve and to direct air from the air intake system to the humidity sensor. The controller may include further instructions to, if degradation of the humidity sensor is not indicated, adjust an engine operating parameter based on output of the humidity sensor when the air from the air intake system is directed to the humidity sensor.

The system may further comprise a third valve configured to selectively supply air from downstream of an air conditioning system evaporator to the pump, and the controller may include instructions to close the first valve and open the third valve and operate the pump to direct air from downstream of the air conditioning system evaporator to the humidity sensor. The controller may include instructions to indicate degradation of the humidity sensor if humidity measured by the humidity sensor does not decrease responsive to the air from downstream of the air conditioning system evaporator being directed to the humidity sensor.

Another embodiment refers to a method comprising, during a first condition, measuring humidity of a first air flow in an air intake system by directing the first air flow to a humidity sensor, during a second condition, measuring humidity of a second air flow in an air conditioning system by pumping the second air flow to the humidity sensor, and if the humidity of the first air flow differs from the humidity of the second air flow by less than a threshold amount, indicating humidity sensor degradation.

The first condition may comprise air from an engine air intake system being directed to the humidity sensor, and the second condition may comprise air from downstream of an air conditioning system evaporator being directed to the humidity sensor. The second air flow may be at a designated humidity, and the second condition may further comprise the humidity of the first air flow being greater than the designated humidity.

The method may further comprise during a third condition, measuring humidity of a third air flow pumped from a chamber housing windshield washer fluid to the humidity chamber, and if the humidity of the first air flow differs from the humidity of the third air flow by less than a threshold amount, indicating humidity sensor degradation. The method may further comprise during the first condition, adjusting an engine operating parameter based on the humidity of the first air flow.

It will be appreciated that the configurations and methods disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
adjusting an engine operating parameter based on humidity of a first gas flow measured by a humidity sensor; and
indicating degradation of the humidity sensor if a humidity of a second, different, gas flow measured by the humidity sensor does not change by an expected amount from the humidity measured of the first gas flow, the second gas flow determined to have a known different humidity from the first gas flow,
wherein the first gas flow comprises air from an engine air intake system, wherein a composition of the second gas flow is different from the first gas flow, wherein the second gas flow comprises crankcase gas from a crankcase vent tube, and wherein an expected humidity is at or near maximum humidity.

2. The method of claim 1, wherein adjusting an engine operating parameter comprises adjusting an amount of exhaust gas recirculated from an engine exhaust to an engine intake.

3. A system comprising:
an engine coupled to an intake system and an exhaust system;
a humidity sensor; and
a controller including instructions to:

during a first condition when the humidity sensor is exposed to a first gas flow, adjust an engine operating parameter based on output of the humidity sensor; and during a second condition when the humidity sensor is exposed to a second, different, gas flow with a different composition than the first gas flow, indicate degradation of the humidity sensor if output of the humidity sensor does not change by an expected output when a composition of measured gas flowing past the sensor changes from a composition of the first gas to the composition of the second gas, wherein:

the humidity sensor is positioned in the intake system downstream of an air intake system throttle, the first condition comprises the air intake system throttle being in a fully open position, the first gas flow comprises intake air at barometric pressure, the second condition comprises the air intake system throttle being in a closed or partially closed position, and the second gas flow comprises intake air at less than barometric pressure.

4. A method, comprising:

adjusting an engine operating parameter based on humidity of a first gas flow measured by a humidity sensor; and indicating degradation of the humidity sensor if a humidity of a second, different, gas flow measured by the humidity sensor does not change by an expected amount from the humidity measured of the first gas flow, the second gas flow determined to have a known different humidity from the first gas flow, wherein the first gas flow comprises air from an air intake system, exhaust gas recirculation system, and crankcase ventilation system, wherein the second gas flow comprises crankcase gas and air from the air intake system, and wherein the expected humidity change is determined to change to at or near maximum humidity, wherein a composition of the second gas flow is different from the first gas flow, wherein degradation of the humidity sensor is determined if output of the humidity sensor does not change by an expected amount when a composition of the gas flowing past the humidity sensor changes.

5. The method of claim 4, wherein adjusting an engine operating parameter comprises adjusting an amount of exhaust gas recirculated from an engine exhaust to an engine intake.

6. A system comprising:

an engine coupled to an intake system and an exhaust system;

a humidity sensor; and a controller including instructions to:

during a first condition when the humidity sensor is exposed to a first gas flow, adjust an engine operating parameter based on output of the humidity sensor; and during a second condition when the humidity sensor is exposed to a second, different, gas flow with a different composition than the first gas flow, indicate degradation of the humidity sensor if output of the humidity sensor does not change by an expected output when composition of measured gas flowing past the sensor changes from a composition of the first gas to the composition of the second gas, wherein:

the humidity sensor is positioned in a passage fluidically coupled to an intake passage upstream of an air intake system throttle and the intake passage downstream of a compressor outlet, the first condition comprises intake manifold pressure less than barometric pressure, the first gas flow comprises intake air, the second condition comprises intake manifold pressure greater than barometric pressure, and the second gas flow comprises intake air and exhaust gas.

7. The system of claim 6, wherein the second gas flow further comprises crankcase gas.

8. A system comprising:

an engine coupled to an intake system and an exhaust system;

a humidity sensor; and a controller including instructions to:

during a first condition when the humidity sensor is exposed to a first gas flow, adjust an engine operating parameter based on output of the humidity sensor; and during a second condition when the humidity sensor is exposed to a second, different, gas flow with a different composition than the first gas flow, indicate degradation of the humidity sensor if output of the humidity sensor does not change by an expected output when composition of measured gas flowing past the sensor changes from a composition of the first gas to the composition of the second gas, wherein:

the humidity sensor is positioned in a passage fluidically coupled to an intake passage downstream of a compressor outlet and an exhaust passage downstream of a turbine outlet, the first condition comprises intake manifold pressure greater than barometric pressure, the first gas flow comprises intake air and exhaust gas, the second condition comprises intake manifold pressure less than barometric pressure, and the second gas flow comprises exhaust gas.

* * * * *